United States Patent
Kobayashi et al.

(10) Patent No.: US 9,615,774 B2
(45) Date of Patent: Apr. 11, 2017

(54) $CO_2$ SENSOR AND $CO_2$ MEASURING APPARATUS

(75) Inventors: Naoki Kobayashi, Tokyo (JP);
Masayuki Inoue, Tokyo (JP);
Hidetoshi Dainobu, Tokyo (JP);
Toshiki Aoki, Tokyo (JP); Kumi Sugiyama, Tokyo (JP); Iwao Takahashi, Tokyo (JP); Kazumasa Ito, Tokyo (JP); Takashi Usuda, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 13/526,959

(22) Filed: Jun. 19, 2012

(65) Prior Publication Data

US 2012/0330161 A1    Dec. 27, 2012

(30) Foreign Application Priority Data

Jun. 24, 2011 (JP) ................... 2011-141059

(51) Int. Cl.
*A61B 5/08* (2006.01)
*A61B 5/00* (2006.01)
*A61B 5/083* (2006.01)

(52) U.S. Cl.
CPC ............ *A61B 5/082* (2013.01); *A61B 5/0075* (2013.01); *A61B 5/0836* (2013.01); *A61B 5/6803* (2013.01); *A61B 5/6814* (2013.01)

(58) Field of Classification Search
CPC ..... A61B 5/0075; A61B 5/082; A61B 5/0836; A61B 5/6803; A61B 5/6814

USPC ................. 600/407, 473, 311, 532
See application file for complete search history.

(56) References Cited

U.S. PATENT DOCUMENTS

| 4,728,499 | A | * | 3/1988 | Fehder ............................ 422/401 |
| 5,311,875 | A | * | 5/1994 | Stasz .................... A61B 5/0878 600/529 |
| 5,660,168 | A | * | 8/1997 | Ottosson et al. ......... 128/200.24 |
| 5,857,460 | A | * | 1/1999 | Popitz ....................... 128/206.21 |
| 6,039,697 | A | * | 3/2000 | Wilke et al. ................... 600/532 |
| 6,379,312 | B2 | * | 4/2002 | O'Toole ......................... 600/529 |
| 7,004,168 | B2 | * | 2/2006 | Mace et al. .............. 128/206.21 |
| 2002/0122746 | A1 | | 9/2002 | Yamamori et al. |
| 2003/0199780 | A1 | * | 10/2003 | Page ............................. 600/538 |
| 2004/0206907 | A1 | | 10/2004 | Yamamori et al. |

(Continued)

FOREIGN PATENT DOCUMENTS

| JP | 63-75541 A | 4/1988 |
| JP | 6-249850 A | 9/1994 |

(Continued)

OTHER PUBLICATIONS

Japanese Office Action for the related Japanese Patent Application No. 2011-141059 dated Feb. 25, 2014.

*Primary Examiner* — Katherine Fernandez
(74) *Attorney, Agent, or Firm* — Pearne & Gordon LLP

(57) ABSTRACT

A $CO_2$ sensor includes: a sensing portion operable to change in color in accordance with a $CO_2$ partial pressure in expiration from at least one of nares and a mouth of a living body; and a mounting member adapted to hold the sensing portion at a position where the expiration from the at least one of the nares and the mouth impinges on the sensing portion.

6 Claims, 15 Drawing Sheets

(56) References Cited

U.S. PATENT DOCUMENTS

| | | | |
|---|---|---|---|
| 2004/0230108 A1* | 11/2004 | Melker | A61B 5/0873 600/340 |
| 2004/0233058 A1* | 11/2004 | Dodds | A61B 5/0002 340/573.1 |
| 2006/0247551 A1 | 11/2006 | Yamamori et al. | |
| 2007/0199567 A1 | 8/2007 | Kanzer | |
| 2008/0076993 A1* | 3/2008 | Ostrowski | 600/341 |
| 2008/0091090 A1* | 4/2008 | Guillory | A61B 5/0478 600/301 |
| 2009/0088657 A1* | 4/2009 | Yamamori et al. | 600/532 |
| 2009/0255535 A1 | 10/2009 | Kanzer | |
| 2011/0094513 A1 | 4/2011 | Takatori et al. | |
| 2011/0218451 A1* | 9/2011 | Lai | A61F 5/56 600/533 |
| 2012/0160246 A1* | 6/2012 | Nguyen et al. | 128/206.19 |
| 2013/0000642 A1* | 1/2013 | Fearnot et al. | 128/204.15 |

FOREIGN PATENT DOCUMENTS

| | | |
|---|---|---|
| JP | 10-248826 A | 9/1998 |
| JP | 2003-315264 A | 11/2003 |
| JP | 2004-321721 A | 11/2004 |
| JP | 3139399 U | 2/2008 |
| JP | 2010-516298 A | 5/2010 |
| JP | 2011-115543 A | 6/2011 |

* cited by examiner

FIG. 3
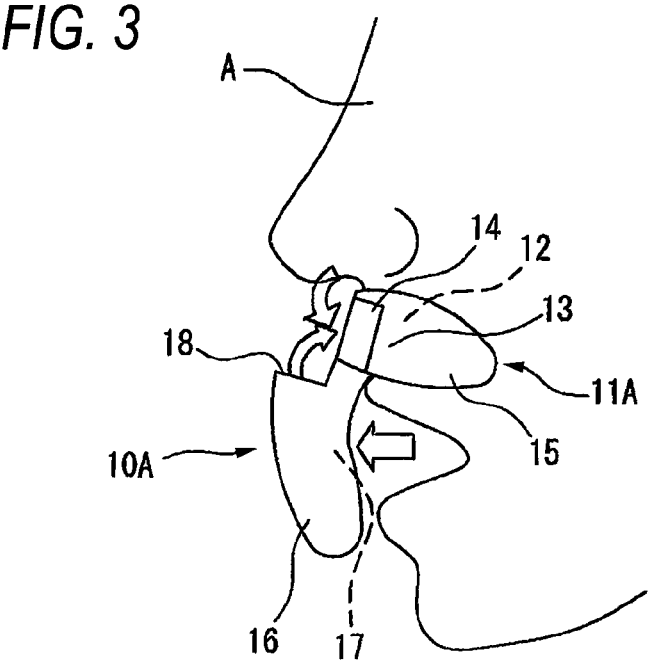
FIG. 4A
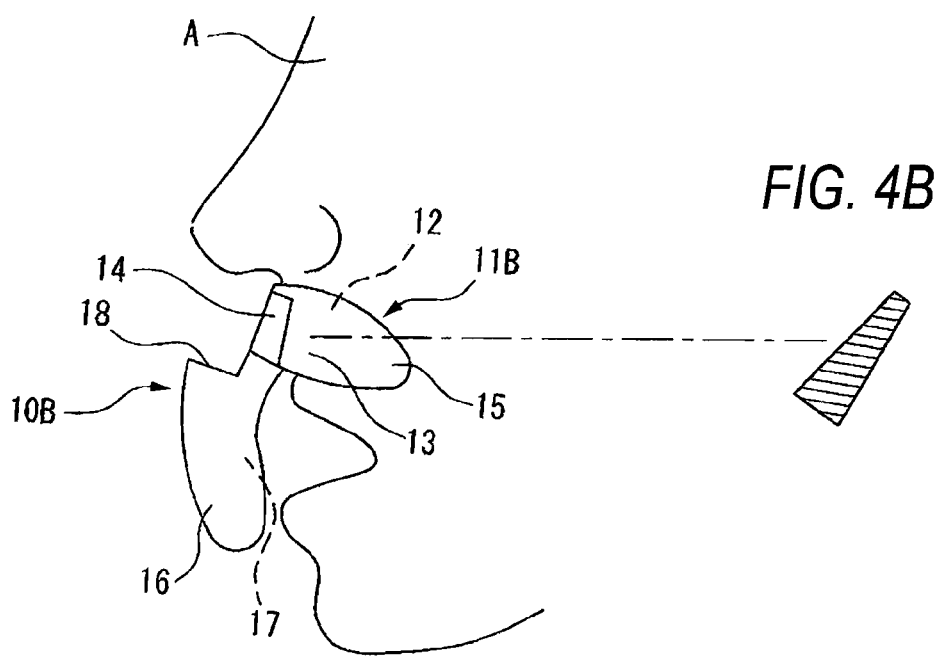
FIG. 4B

CO₂ SENSOR AND CO₂ MEASURING APPARATUS

BACKGROUND OF THE INVENTION

The present invention relates to a $CO_2$ sensor for measuring the presence of the respiration and the $CO_2$ partial pressure in the expiration, and also to a $CO_2$ measuring apparatus including the $CO_2$ sensor.

As a CO2 sensor for measuring the $CO_2$ partial pressure in the expiration, there are a sensor based on the infrared spectroscopy method which uses infrared absorption of $CO_2$ (see Patent Reference 1), that based on the dye method in which a pH change of an electrolytic solution caused by $CO_2$ is detected as a color change of a pigment (see Patent References 2 and 3), and the like.

The sensor of the infrared spectroscopy method disclosed in Patent Reference 1 can measure the partial pressure without intubation, but is expensive, and has limitations in miniaturization and low power consumption. The sensors of the dye method disclosed in Patent References 2 and 3 are economical and have advantages that miniaturization and low power consumption are enabled. However, the sensors are of a type in which it is used while being disposed in a pipe connected to an intubation tube. Therefore, the sensors cannot measure the partial pressure without intubation, and hence their application range is limited.

(Patent Reference 1) JP-A-2003-315264
(Patent Reference 2) JP-A-06-249850
(Patent Reference 3) JP-A-63-75541

SUMMARY

It is therefore an object of the invention to provide a $CO_2$ sensor and $CO_2$ measuring apparatus which are economical and small in size, which can measure the presence of the respiration and the $CO_2$ partial pressure at a low power consumption, which can be widely applied to respiration management of the patient, and which can largely contribute to safety of the patient.

In order to achieve the object, according to the invention, there is provided a $CO_2$ sensor comprising: a sensing portion operable to change in color in accordance with a $CO_2$ partial pressure in expiration from at least one of nares and a mouth of a living body; and a mounting member adapted to hold the sensing portion at a position where the expiration from the at least one of the nares and the mouth impinges on the sensing portion.

The mounting member may be adapted to hold the sensing portion on a philtrum of the living body.

The mounting member may include a projecting piece, the sensing portion may be disposed in the projecting piece, and when the mounting member is attached to the living body, the mounting member may be adapted to hold the sensing portion between the nares and the mouth of the living body.

The mounting member may include an airflow path which guides the expiration from the mouth to the sensing portion.

The mounting member may be included in a mask-like air permeable member which is adapted to be held on a face of the living body.

The mounting member may be included in an oxygen mask, and the sensing portion may be disposed in an inner side of the oxygen mask.

In order to achieve the object, according to the invention, there is also provided a $CO_2$ measuring apparatus comprising: the $CO_2$ sensor; a light source operable to emit a light signal toward the sensing portion; a light receiver operable to receive a light signal from the sensing portion; and a $CO_2$ measuring unit operable to perform a $CO_2$ measurement based on the light signal received by the light receiver.

The light signal received by the light receiver may be a light signal reflected from or transmitted through the sensing portion.

The light signal emitted from the light source may include at least two kinds of light signals having different wavelengths.

An optical fiber for conducting light may be disposed at least one of an area from the light source to the sensing portion and an area from the sensing portion to the light receiver.

BRIEF DESCRIPTION OF THE DRAWINGS

FIG. 3 is a diagram showing the second embodiment of the $CO_2$ sensor of the invention.

FIGS. 4A and 4B are diagrams showing a modification of the second embodiment of the $CO_2$ sensor of the invention.

DETAILED DESCRIPTION OF EMBODIMENTS

Figure 1:
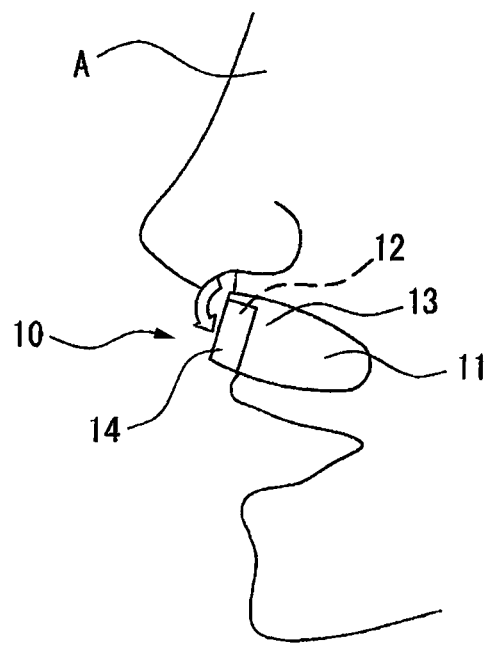
FIG. 1 is a diagram showing a first embodiment of the $CO_2$ sensor of the invention.

Hereinafter, embodiments of the $CO_2$ sensor and $CO_2$ measuring apparatus of the invention will be described with reference to the accompanying drawings. In the figures, the identical components are denoted by the same reference numerals, and duplicated description will be omitted. FIG. 1 shows a first embodiment of the $CO_2$ sensor of the invention. The $CO_2$ sensor 10 has a mounting member 11 configured by a tape or sheet which is substantially identical in configuration to a backing strip (a tape) of an adhesive bandage with a pack, and which has an elongated shape. An adhesive agent is applied to a first surface 12 through which the mounting member 11 is to be stuck to a living body A.

A sensing portion 14 is disposed in a middle portion of a second surface 13 which is opposite to the first surface 12 of the mounting member 11. The sensing portion 14 changes in color in accordance with the $CO_2$ partial pressure in the expiration. For example, the sensing portion can be configured by causing a chemical solution disclosed in Patent Reference 2 or 3 or the like to be carried in cloth, paper, or the like functioning as a carrier. Alternatively, the chemical solution may be carried in the mounting member 11. The size of the sensing portion 14 may be set so that the sensing portion just fits on the philtrum. The sensing portion 14 is detachably disposed in the vicinity of the nares by the mounting member 11.

When the $CO_2$ sensor 10 of the first embodiment is placed and held on the philtrum as described above, $CO_2$ in the expiration ejected from the nares reaches the sensing portion 14, and the sensing portion 14 changes in color in accordance with the $CO_2$ partial pressure. Therefore, the presence of the respiration and the concentration of $CO_2$ contained in the expiration can be approximately measured by viewing the color change of the sensing portion 14. The thus configured $CO_2$ sensor 10 is suitably used in respiration management of a neonate or the like who breathes through only the nose.

Figure 2:
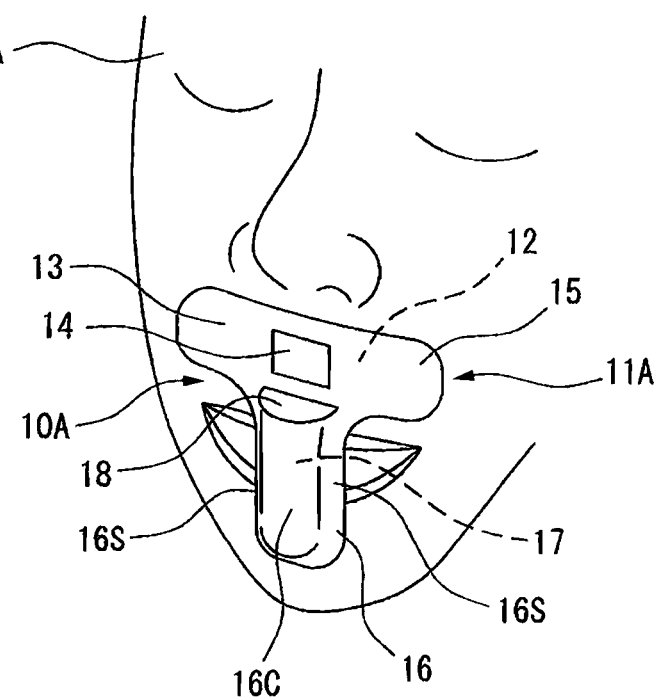
FIG. 2 is a diagram showing a second embodiment of the $CO_2$ sensor of the invention.

FIGS. 2 and 3 show the configuration of a $CO_2$ sensor 10A of a second embodiment. A mounting member 11A of the $CO_2$ sensor 10A has: an adhesive portion 15 which longitudinally extends about the philtrum in a band-like manner above the upper lip; and a mouth cover 16 which is integrated with the adhesive portion 15, which has a rectangular or oval plan shape, and which is formed so as to downward extend.

The adhesive portion 15 is formed by a thin resin having a backing strip-like shape. An adhesive agent is applied to the first surface 12 which is to be stuck to the living body A. The sensing portion 14 is stuck to a middle portion of the second surface 13 which is opposite to the first surface 12.

The mouth cover 16 may be formed by a resin which is thicker than the adhesive portion 15, and is disposed in a state where the cover hangs substantially perpendicularly from the adhesive portion 15 toward the mouth. The mouth cover 16 is configured so that the cover extends vertically while a middle portion 16C is projected toward the side opposite to the living body side, and the both side edges 16S, 16S of the middle portion 16C are inclined so as to become closer to the mouth.

An airflow path 17 which is a groove is vertically formed in the living body side of the mouth cover 16, and an opening 18 which faces the sensing portion 14 is bored in an upper end portion of the airflow path 17. Because of the above-described configuration, the airflow path 17 has a function of guiding the expiration ejected from the mouth to the sensing portion 14.

As described above, the $CO_2$ sensor 10A of the second embodiment is placed and held on the philtrum, thereby allowing $CO_2$ in the expiration ejected from the nares and the mouth to reach the sensing portion 14, so that the sensing portion 14 changes in color. Therefore, the presence of the respiration and the concentration of $CO_2$ contained in the expiration can be approximately measured by viewing the color change of the sensing portion 14. The thus configured $CO_2$ sensor 10A is suitably used in respiration management of an adult or the like who breathes through both the nares and the mouth. However, the sensor can be applied also to a neonate who breathes only through the nose.

FIGS. 4A and 4B show a modification of the second embodiment. The $CO_2$ sensor 10B is different from the second embodiment in that, in the adhesive portion 15 of the mounting member 11B, at least the sensing portion 14 has a shape which, as shown in FIG. 4B, is thick on the lip side, and thinner as further advancing toward the nose side. Alternatively, the whole adhesive portion 15 may be configured as described above. In the thus configured $CO_2$ sensor 10B, the sensing portion 14 is to be attached to the living body A in the state where the sensing portion 14 is directed more upwardly as compared with the embodiment of FIGS. 2 and 3, and hence the expiration ejected from the nares easily impinges on the sensing portion 14, so that the accuracy of detection of $CO_2$ from the nares can be improved.

Figure 5:
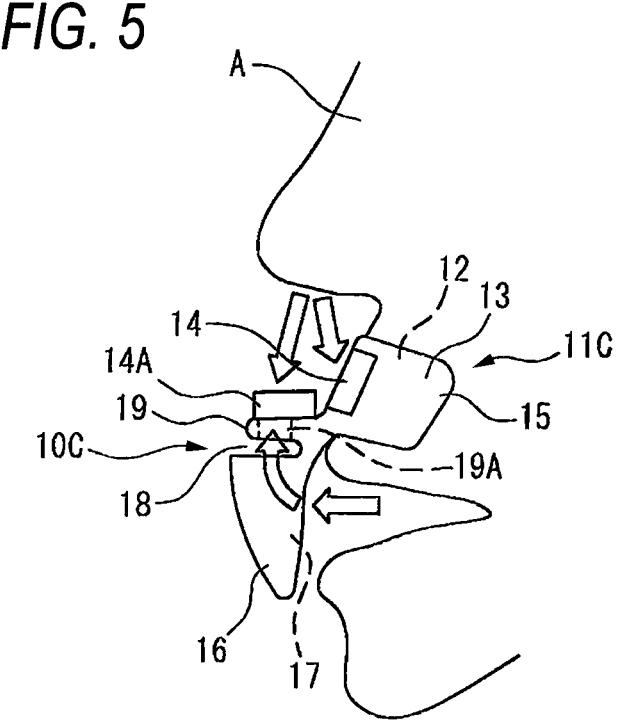
FIG. 5 is a diagram showing a third embodiment of the $CO_2$ sensor of the invention.

FIG. 5 shows a third embodiment. In the $CO_2$ sensor 10C, a mounting member 11C has a configuration which is basically identical to the mounting member in the second embodiment. In the embodiment, the member has a projecting piece 19 which is forward projected from a part of the adhesive portion 15. Specifically, the projecting piece 19 is forward projected from a joining portion between the adhesive portion 15 and the mouth cover 16, and formed so as to be located above the opening 18. A through hole 19A having a diameter which is approximately equal to that of the opening 18 is bored in the projecting piece 19. Above the through hole 19A, a sensing portion 14A having the same configuration as the sensing portion 14 is placed so as to close the through hole 19A. $CO_2$ in the expiration ejected from the mouth reaches the sensing portion 14A from the airflow path 17 through the opening 18 and the through hole 19A, thereby causing the sensing portion 14A to change in color. $CO_2$ in the expiration ejected from the nares reaches the sensing portion 14A placed on the projecting piece 19, and the sensing portion 14 disposed in the adhesive portion 15, thereby causing the sensing portions 14, 14A to change in color. According to the embodiment, the sensing portions 14, 14A in the two places can adequately measure $CO_2$.

Figure 6:
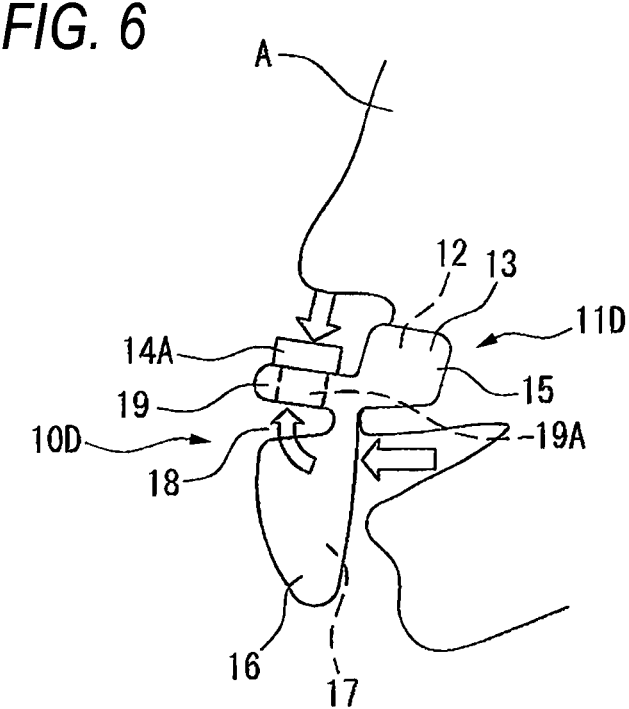
FIG. 6 is a diagram showing a modification of the third embodiment of the $CO_2$ sensor of the invention.

FIG. 6 shows a modification of the third embodiment of FIG. 5. In the $CO_2$ sensor 10D, the sensing portion 14 disposed in the $CO_2$ sensor 10C of the third embodiment of FIG. 5 is omitted, and the other configuration is similar to that of the $CO_2$ sensor 10C. In the modification, $CO_2$ in the expiration ejected from the nares and the mouth reaches the sensing portion 14A placed on the projecting piece 19, thereby causing the sensing portion 14A to change in color.

Figure 7:
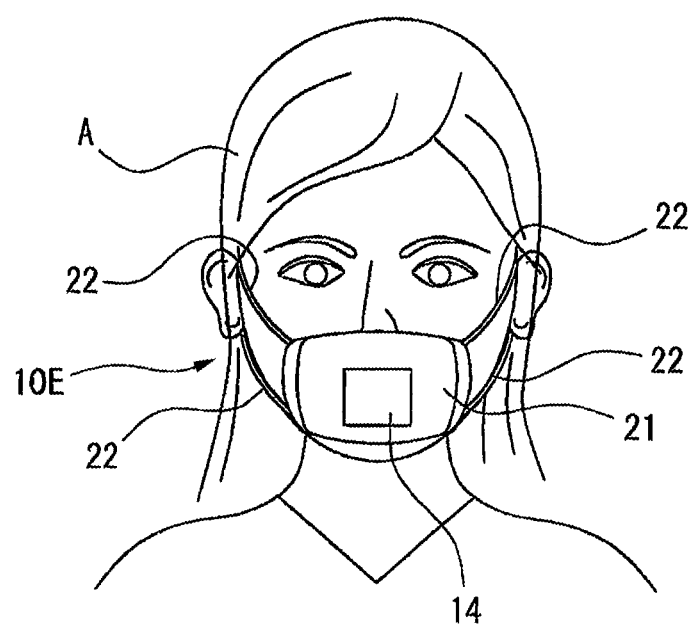
FIG. 7 is a diagram showing a fourth embodiment of the $CO_2$ sensor of the invention.

FIG. 7 shows a $CO_2$ sensor 10E of a fourth embodiment. The $CO_2$ sensor 10E has: a mask 21 which is configured by an air permeable sheet such as a woven fabric or a nonwoven fabric, and which functions as a mounting member; and the sensing portion 14 which has been described above. The mask 21 has a plan shape which is substantially rectangular. Strings 22 which are to be looped over the ears to hold the mask 21 elongate from two sides which, when the mask 21 is attached, are located on the cheeks, respectively. The strings 22 can be adjusted in length so that, when the mask 21 is attached by the strings 22, the sensing portion 14 is located in front of the mouth and the nose. The air resistance of the air permeable sheet constituting the mask 21 is set to 4 $mmH_2O/cm^2$ or less.

According to the embodiment, cardiopulmonary resuscitation can be executed in a state where the $CO_2$ sensor 10E is attached to the living body (patient) A, and the situation such as that the living body (patient) A resumes respiration can be detected by observing the color change of the sensing portion 14. This is convenient. Moreover, mouth-to-mouth ventilation can be applied through the mask 21 in a non-contact manner, and therefore infection can be prevented.

Figure 8A:
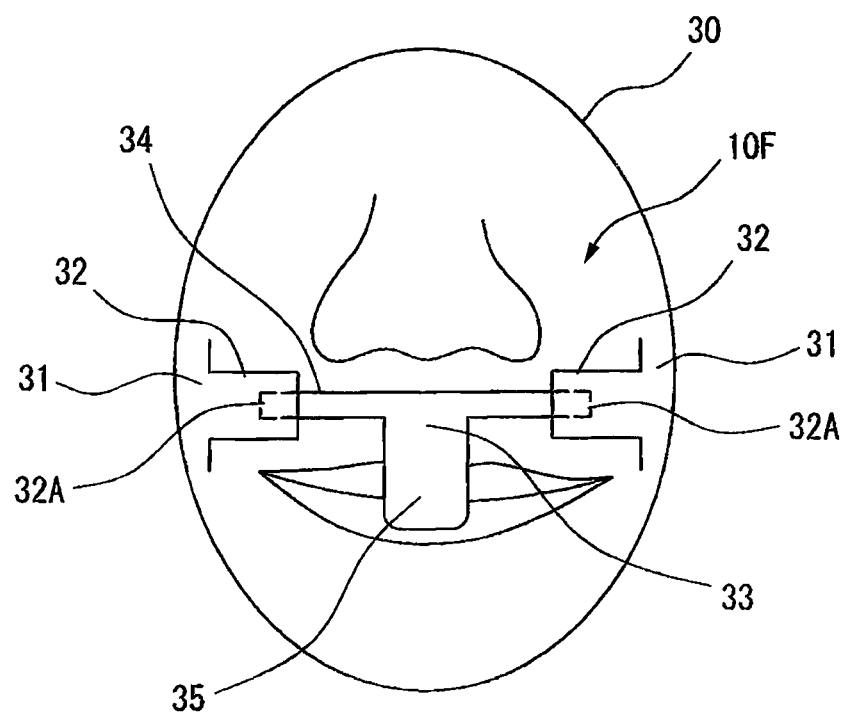
FIGS. 8A and 8B are diagrams showing a fifth embodiment of the $CO_2$ sensor of the invention.
Figure 8B:
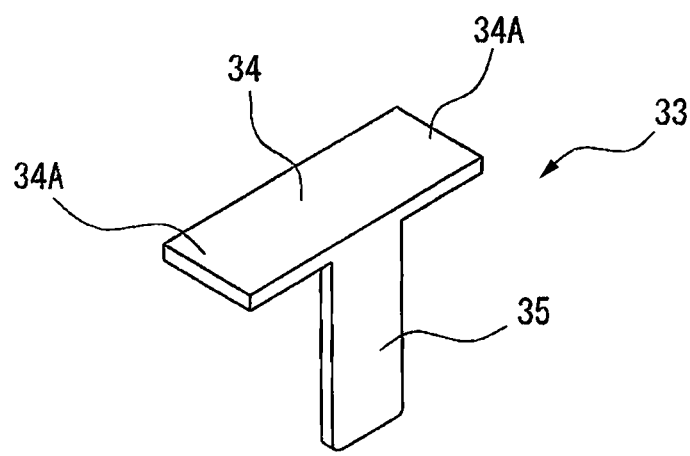

FIGS. 8A and 8B show a $CO_2$ sensor 10F of a fifth embodiment. The $CO_2$ sensor 10F includes a mounting member 31 disposed on, for example, the inner wall of an oxygen mask 30 which is transparent, and which has a cup-like shape. The mounting member 31 is configured by support rod members 32, 32 which are projected and opposed to each other so as to sandwich the philtrum from the both lateral sides. As shown in FIG. 8B, a sensing portion 33 has a shape in which two rectangular plates are perpendicularly joined to each other, and is configured so as to, in a similar manner as the above-described sensing portion 14, change in color in accordance with the $CO_2$ partial pressure in the expiration. The sensing portion can be configured by causing a chemical solution or the like to be carried in cloth, paper, or the like functioning as a carrier. The oxygen mask 30 is attached by strings or bands which are not shown, in a state where the mask encapsulates the mouth and the nose, and oxygen is sent the mask from an oxygen bottle or the like through a tube (not shown).

The sensing portion 33 includes a first sensing portion 34 which corresponds to nasal expiration, and a second sensing portion 35 which perpendicularly extends from the middle side of the first sensing portion 34, and which corresponds to oral expiration. Gripping portions 32A, 32A configured by holes or grooves into which the both ends 34A, 34A of the first sensing portion 34 are to be fitted are formed in the opposed surfaces of the support rod members 32, 32. The first sensing portion 34 is used while the both ends 34A, 34A are fitted into the gripping portions 32A, 32A, and, as required, can be used after being replaced with a fresh one. Because of the above-described configuration, the respiratory condition of the living body (patient) A to which the oxygen mask 30 is attached can be observed by a color change of the sensing portion 33, and necessary respiration management can be executed.

Figure 9:
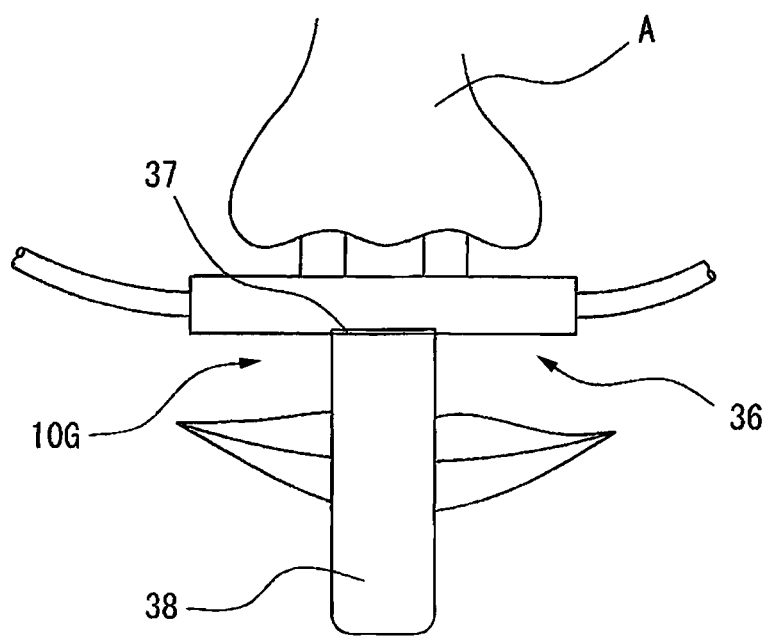
FIG. 9 is a diagram showing a sixth embodiment of the $CO_2$ sensor of the invention.

FIG. 9 shows a $CO_2$ sensor 10G of a sixth embodiment. In the $CO_2$ sensor 10G, a nasal cannula 36 has a mounting member 37. A sensing portion 38 has a shape of a rectangle, and is configured so that, in a similar manner as the above-described sensing portion 14, the color changes in accordance with the $CO_2$ partial pressure in the expiration. The sensing portion can be configured by causing a chemical solution or the like to be carried in cloth, paper, or the like functioning as a carrier.

The mounting member 37 can be configured by a mechanism which grips the upper edge of the sensing portion 38 by elastic means or the like. Alternatively, the mounting member 37 may be an outer wall of a cylinder of the nasal cannula 36, an adhesive agent may be applied to an upper edge of the sensing portion 38 which is opposed to the outer wall, and the sensing portion may be stuck to the outer wall. In the both configurations, the sensing portion 38 is located in front of the mouth of the living body A in a state where the sensing portion is hung from the lowest surface of the cylinder of the nasal cannula 36. $CO_2$ in the expiration ejected from the mouth is blown to the sensing portion 38, and a color change occurs. According to the configuration, the respiratory condition of the patient to whom the nasal cannula 36 is attached can be monitored by a color change of the sensing portion 38, and respiration management can be performed easily and adequately on the patient. As required, also the sensing portion 38 can be used after being replaced with a fresh one.

Figure 10:
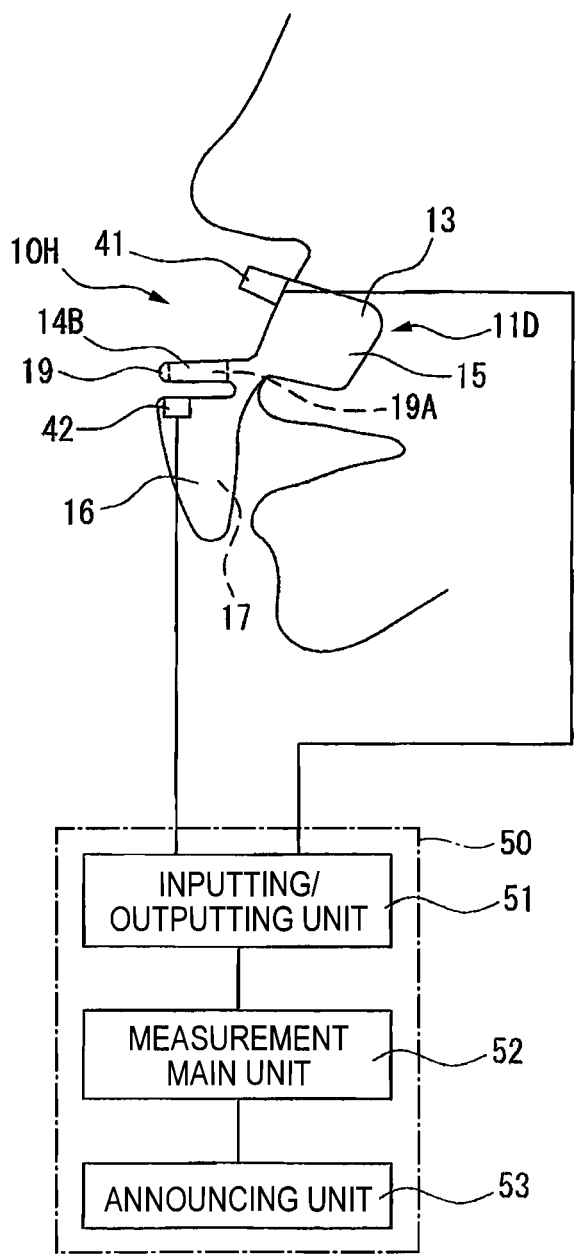
FIG. 10 is a diagram showing a first embodiment of the $CO_2$ measuring apparatus of the invention.

FIG. 10 shows a first embodiment of the $CO_2$ measuring apparatus which is configured by using a $CO_2$ sensor 10H that is substantially identical with the sensor shown in FIG. 6. A sensing portion 14B is detachably fitted to the through hole 19A which is formed in the projecting piece 19. The sensing portion 14B has a configuration similar to the sensing portion 14, and has translucency. A light source 41 configured by a light emitting device such as an LED is attached to the middle of the adhesive portion 15 of a mounting member 11D. The light source 41 emits light (first wavelength light) of at least one wavelength in which the light absorption property is hardly affected by a color change of the sensing portion 14B, and light (second wavelength light) of at least one wavelength in which the light absorption property is susceptible to a color change of the sensing portion 14B.

A light receiver 42 configured by a photosensor or the like is disposed in a tip end portion of the mouth cover 16 which faces the opening 18. The light receiver 42 is disposed at a position which is opposed to the light source 41 via the sensing portion 14B, and the lights emitted from the light source 41 are received by the light receiver 42 through the sensing portion 14B.

The light source 41 and the light receiver 42 are connected to an inputting/outputting unit 51 of a CO2 measuring unit 50. A measurement main unit 52 is connected to the inputting/outputting unit 51 of the CO2 measuring unit 50, and an announcing unit 53 is connected to the measurement main unit 52. In the announcing unit 53, for example, a display device configured by an LCD can be used. The measurement main unit 52 controls the inputting/outputting unit 51 so that the light source 41 emits the lights. The light receiver 42 receives the lights through the sensing portion 14B, and sends photoelectrically converted signals to the inputting/outputting unit 51. A light reception signal corresponding to the first wavelength light, and that corresponding to the second wavelength light reach the inputting/outputting unit 51. The inputting/outputting unit 51 digitizes these signals, and then sends the digitized signals to the measurement main unit 52. The measurement main unit 52 compares the digital signal corresponding to the first wavelength light with that corresponding to the second wavelength light. In order to convert the ratio of the signals to a $CO_2$ amount (ppm), the measurement main unit obtains the $CO_2$ amount by using a table which is previously prepared, and sends the $CO_2$ amount to the announcing unit 53. Consequently, the sensor can be easily placed, and the $CO_2$ amount can be adequately measured.

Figure 11:
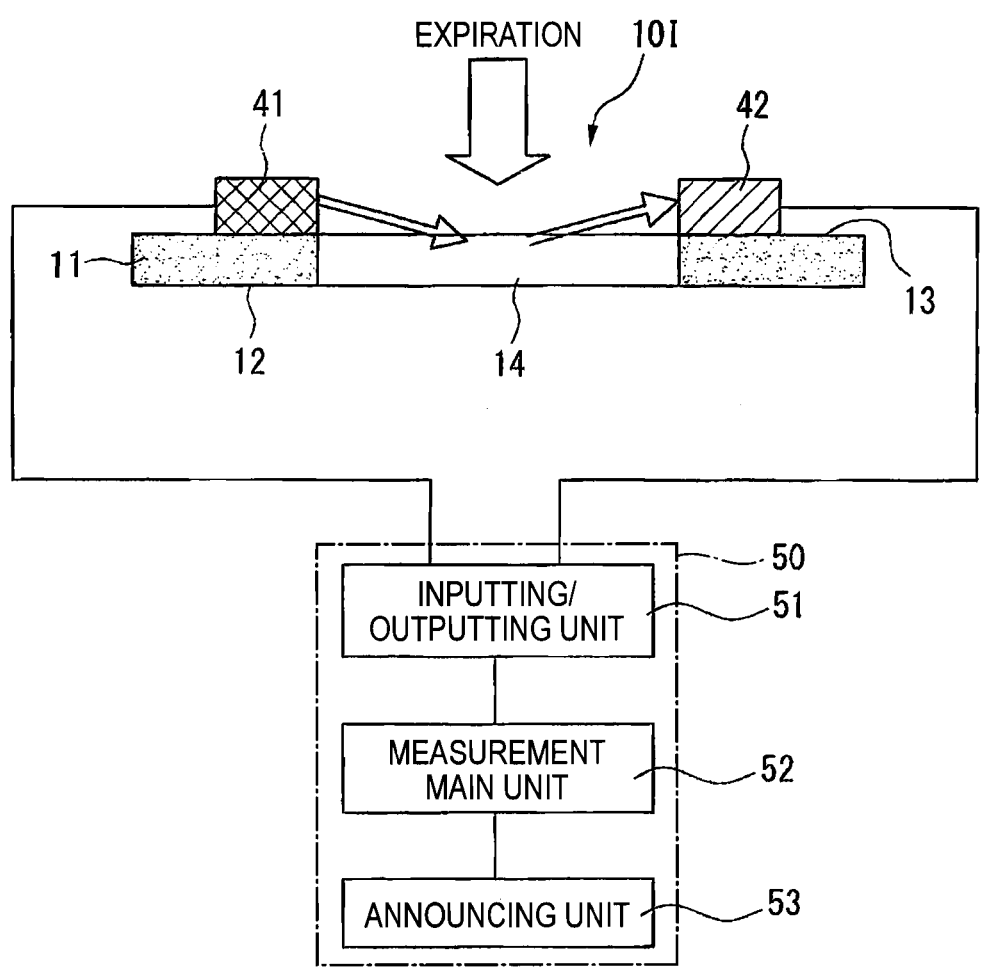
FIG. 11 is a diagram showing a second embodiment of the $CO_2$ measuring apparatus of the invention.

FIG. 11 shows a second embodiment of the $CO_2$ measuring apparatus which is configured by using a $CO_2$ sensor 10I that is substantially identical with the sensor shown in FIG. 1. The sensing portion 14 is detachably embedded in a hole disposed in the mounting member 11 which is configured by a tape or a sheet. The light source 41 and the light receiver 42 are disposed at positions of the second surface 13 on which the expiration ejected from the nares impinges, and which faces the sensing portion 14. The light source 41 and the light receiver 42 are placed so that the lights emitted from the light source 41 are reflected by the sensing portion 14 and then received by the light receiver 42.

The light source 41 and the light receiver 42 are connected to the inputting/outputting unit 51 of the $CO_2$ measuring unit 50. The configuration and operation of the $CO_2$ measuring unit 50 are identical with those of the first embodiment of the $CO_2$ measuring apparatus. Therefore, the $CO_2$ sensor 10I is stuck to the philtrum, and the $CO_2$ amount can be adequately measured.

Figure 12:
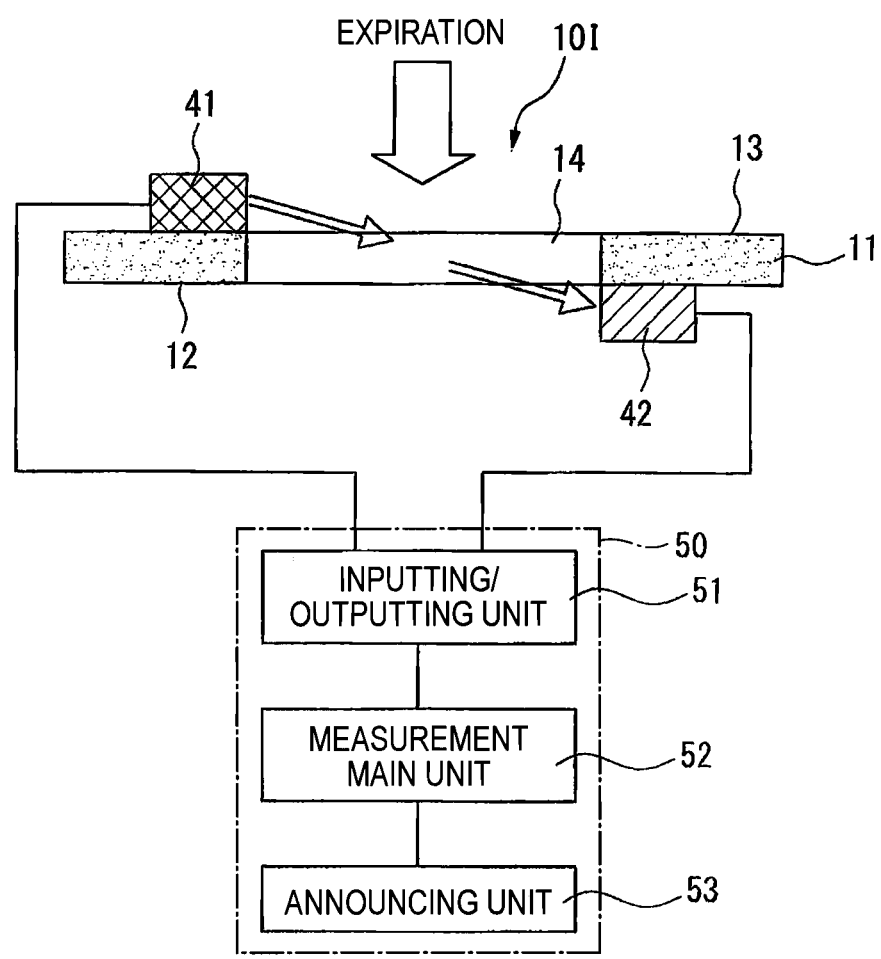
FIG. 12 is a diagram showing a modification of the second embodiment of the $CO_2$ measuring apparatus of the invention.

FIG. 12 shows a modification of the second embodiment of the $CO_2$ measuring apparatus. In the modification, the light receiver 42 is disposed on the first surface 12, and the light source 41 is disposed on the second surface 13. The light source 41 and the light receiver 42 are placed so that the lights emitted from the light source 41 are transmitted through the sensing portion 14 to be received by the light receiver 42. The other configuration is similar to that of the second embodiment of the $CO_2$ measuring apparatus. According to thus configured $CO_2$ measuring apparatus, the $CO_2$ sensor 10I is stuck to the philtrum, and the $CO_2$ amount can be adequately measured.

Figure 13:
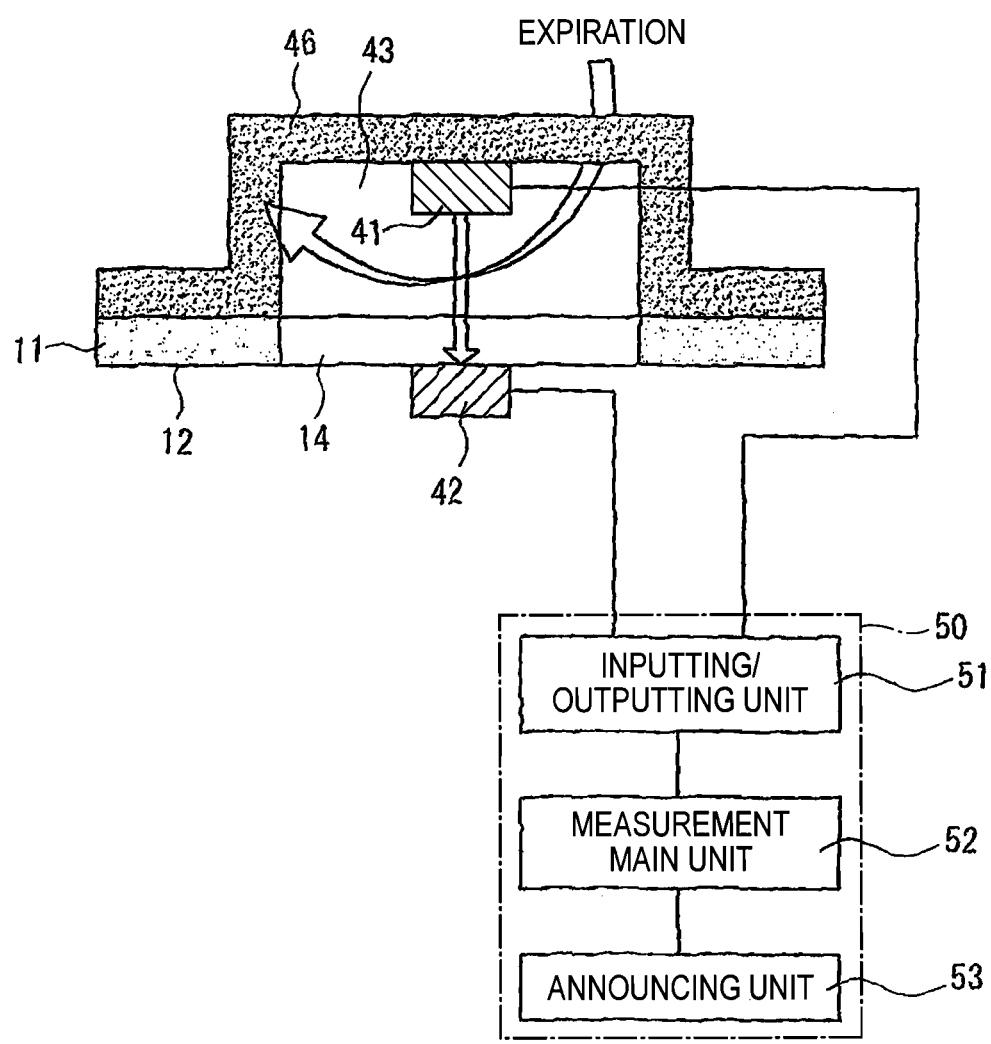
FIG. 13 is a diagram showing a third embodiment of the $CO_2$ measuring apparatus of the invention.

FIG. 13 shows a third embodiment of the $CO_2$ measuring apparatus which is configured by using a $CO_2$ sensor that is substantially identical with the sensor shown in FIG. 1. A hole is formed in the mounting member 11, and the sensing portion 14 is embedded in the hole. An air permeable sheet 46 is stuck to the mounting member 11 to be integrated therewith so that a space 43 is formed in a front portion of the sensing portion 14. The light source 41 is disposed on the wall surface of the sheet 46 in the space 43. The light receiver 42 is disposed in the sensing portion 14 on the side of the first surface 12 of the mounting member 11. The light source 41 and the light receiver 42 are placed so that the lights emitted from the light source 41 are transmitted through the sensing portion 14 to be received by the light receiver 42.

The light source 41 and the light receiver 42 are connected to the CO2 measuring unit 50 in the same manner as FIG. 12. According to the configuration, the side of the first surface 12 of the attaching member 11 is stuck between the nose and the mouth so that the sensing portion 14 is placed on the philtrum. The expiration ejected from the nares and the mouth enters the space 43 through the sheet 46, and impinges on the sensing portion 14, thereby causing the sensing portion 14 to change in color. Light corresponding to the color change is received by the light receiver 42, and the signals in the light receiver 42 are processed in the $CO_2$ measuring unit 50 in a similar manner as described above.

Figure 14A:
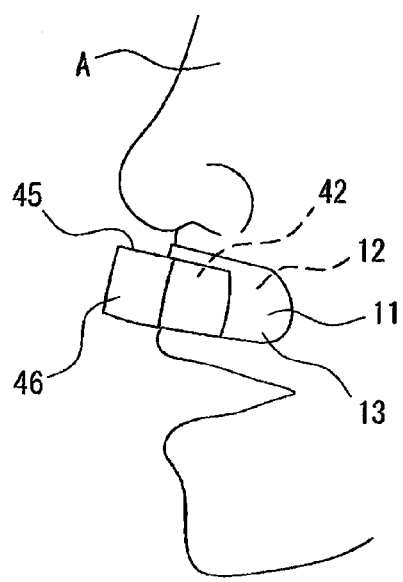
FIGS. 14A and 14B are perspective views showing the configuration of the third embodiment of the $CO_2$ measuring apparatus of the invention.
Figure 14B:
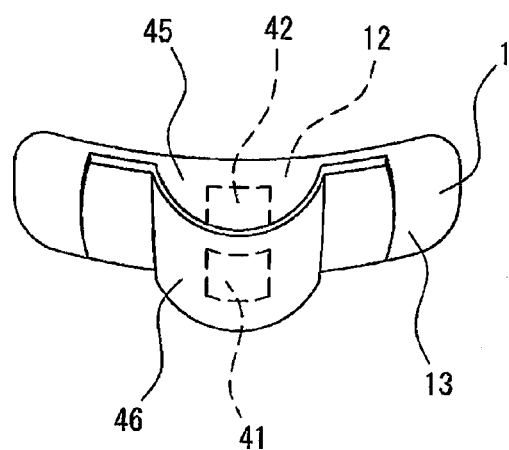
Figure 15A:
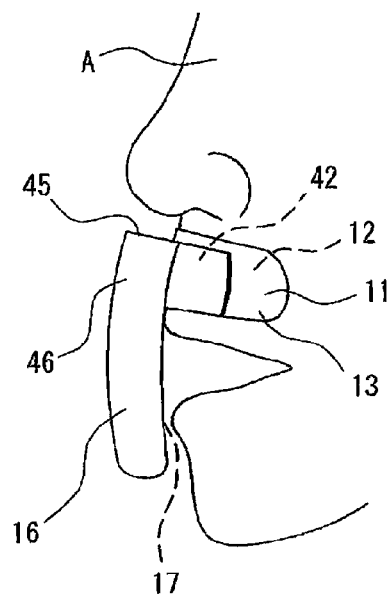
FIGS. 15A and 15B are perspective views showing the configuration of the third embodiment of the $CO_2$ measuring apparatus of the invention.
Figure 15B:
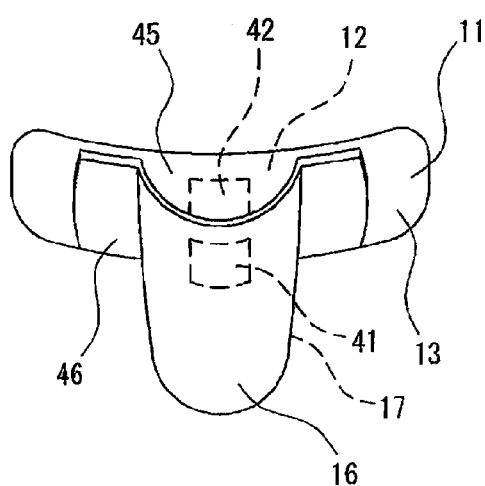

FIGS. 14A and 14B are diagrams of a sensor portion which is in the $CO_2$ measuring apparatus shown in FIG. 13, and which is of a type corresponding to the expiration from the nares, and FIGS. 15A and 15B are diagrams of a sensor portion which is in the $CO_2$ measuring apparatus shown in FIG. 13, and which is of a type corresponding to the expiration from the nares and the mouth. According to thus configured $CO_2$ measuring apparatus, the $CO_2$ sensor is stuck to the philtrum, and the $CO_2$ amount can be adequately measured.

Figure 16:
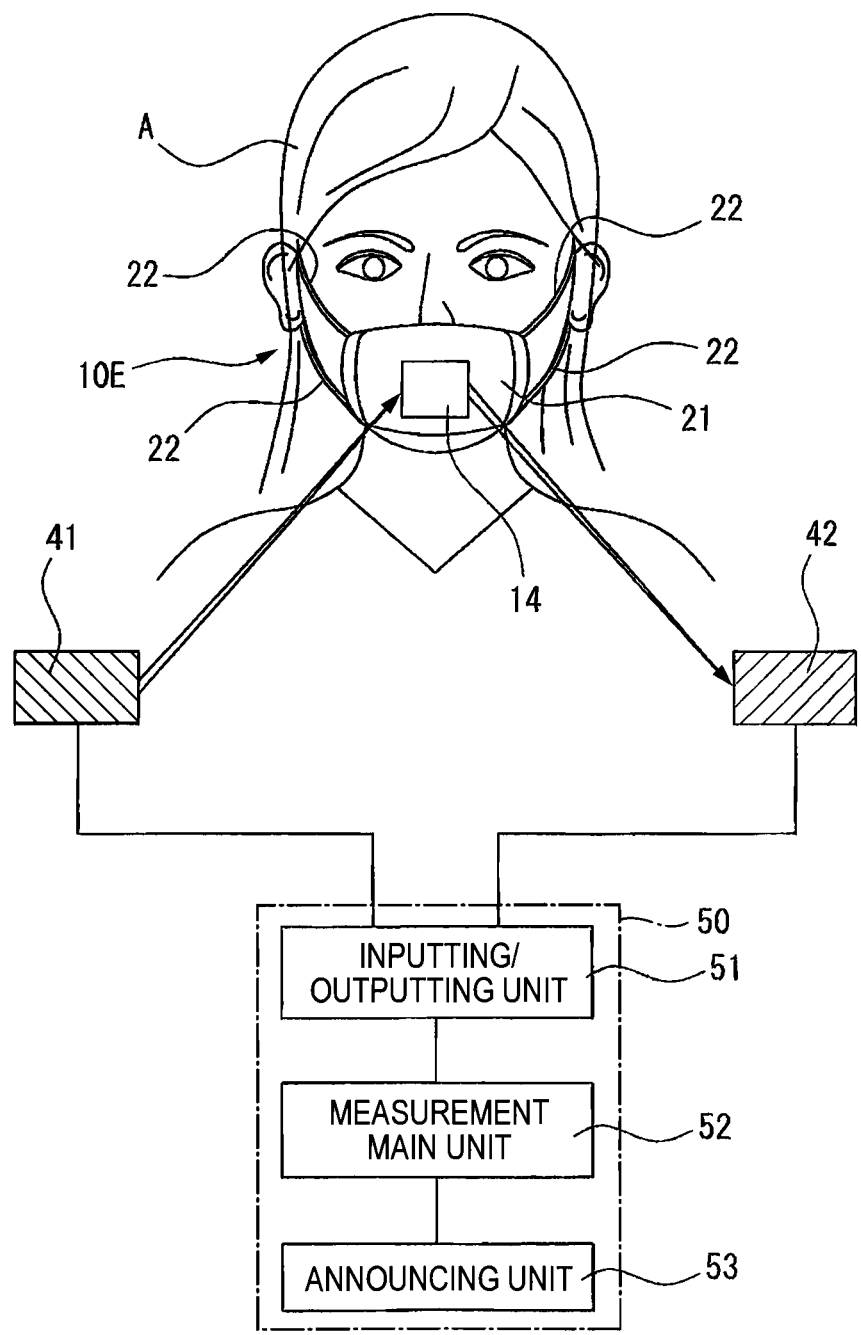
FIG. 16 is a diagram showing a fourth embodiment of the $CO_2$ measuring apparatus of the invention.

FIG. 16 shows a fourth embodiment of the $CO_2$ measuring apparatus which is configured by using the $CO_2$ sensor 10E shown in FIG. 7. The light source 41 is placed in front of the sensing portion 14, and the light receiver 42 is placed so as to receive the lights which are emitted from the light source 41 and reflected by the sensing portion 14. The light source 41 and the light receiver 42 are connected to the $CO_2$ measuring unit 50 which is identical with the above-described $CO_2$ measuring apparatus. Lights corresponding to the color change of the sensing portion 14 are received by the light receiver 42, and the signals in the light receiver 42 are processed in the $CO_2$ measuring unit 50 in a similar manner as described above.

Figure 17:
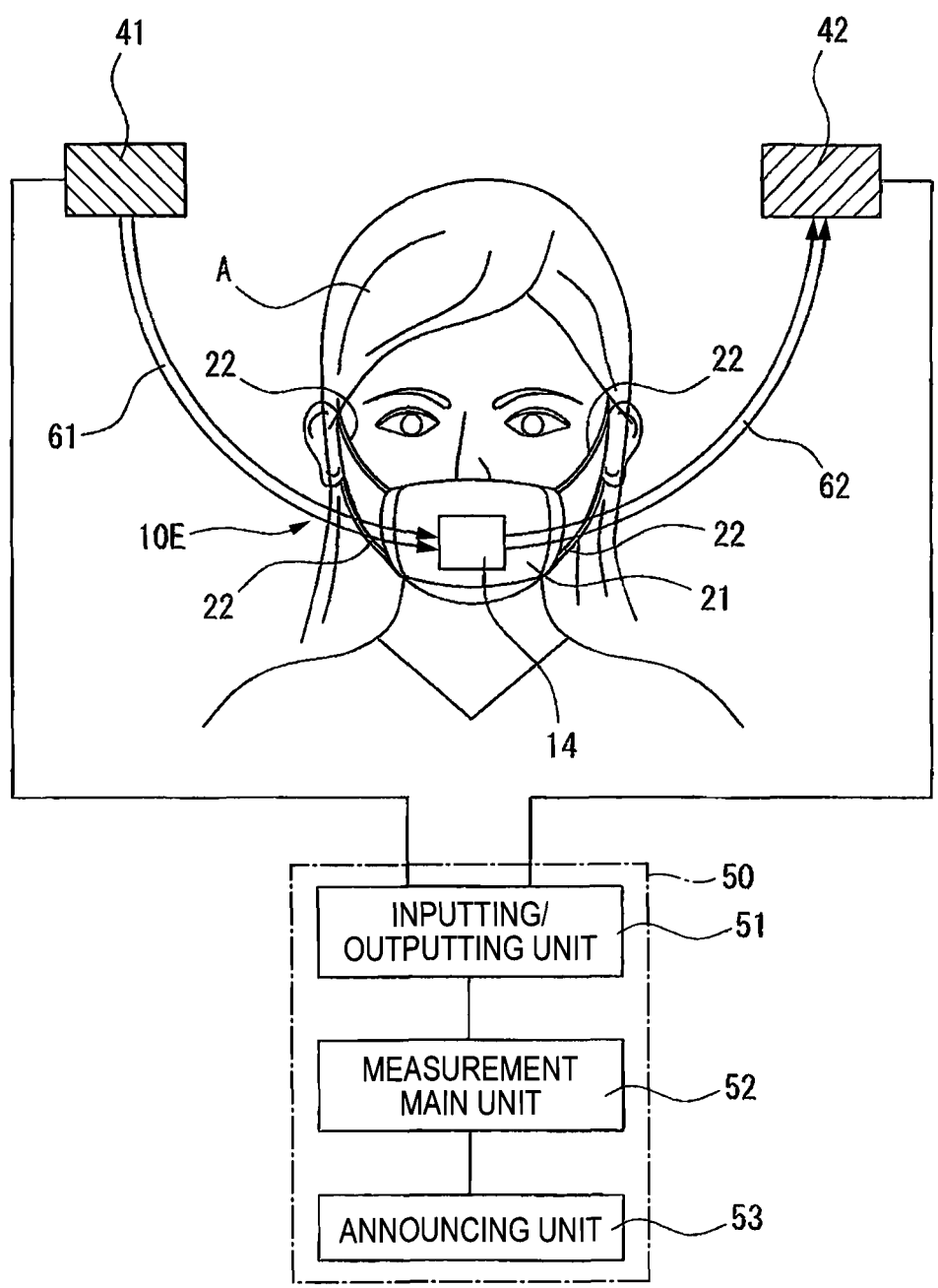
FIG. 17 is a diagram showing a modification of the fourth embodiment of the $CO_2$ measuring apparatus of the invention.

FIG. 17 shows a modification of the $CO_2$ measuring apparatus shown in FIG. 16. In the $CO_2$ measuring apparatus, optical fibers 61, 62 are used as light guiding paths through which the lights are guided in FIG. 16. Namely, the light source 41 is disposed in the light inlet end of the optical fiber 61, and the sensing portion 14 is disposed in the light outlet end of the optical fiber 61. On the other hand, the sensing portion 14 is disposed in the light inlet end of the optical fiber 62, and the light receiver 42 is disposed in the light outlet end of the optical fiber 62. According to the configuration, the apparatus can cope with the situation of a medical facility without limiting the placement positions of the light source 41 and the light receiver 42. The other configuration is similar to that of the embodiment of FIG. 16, and it is possible to achieve similar effects.

Figure 18:
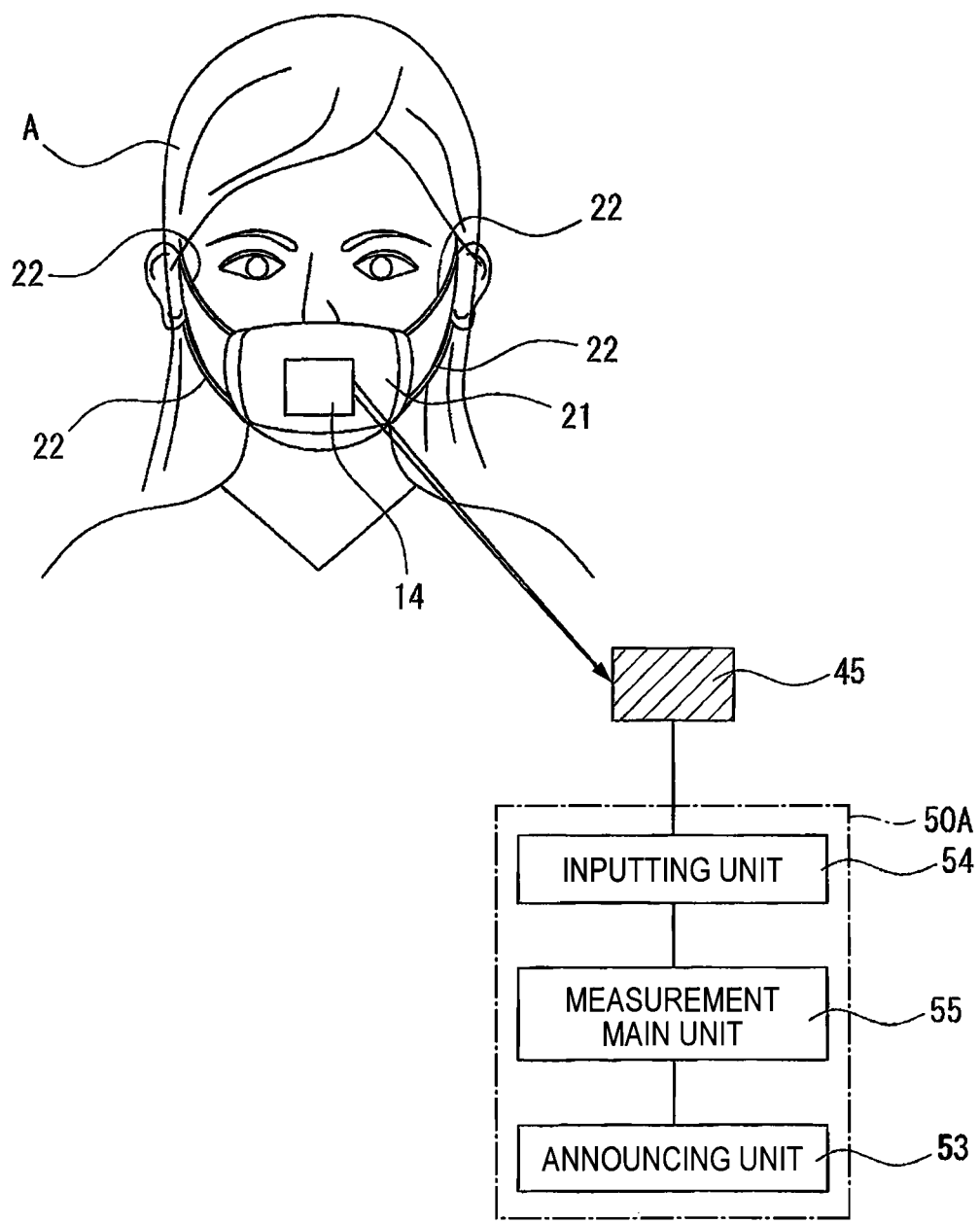
FIG. 18 is a diagram showing a fifth embodiment of the $CO_2$ measuring apparatus of the invention.

FIG. 18 shows a fifth embodiment of the $CO_2$ measuring apparatus which is configured by using the $CO_2$ sensor 10E shown in FIG. 7. In the embodiment, a light receiver 45 is disposed in front of the sensing portion 14. A CCD image sensor or CMOS image sensor which captures the light signals of the sensing portion 14 can be used as the light receiver 45.

The light receiver 45 is connected to an inputting unit 54 of a $CO_2$ measuring unit 50A. A measurement main unit 55 is connected to the inputting unit 54 of the $CO_2$ measuring unit 50A, and the announcing unit 53 is connected to the measurement main unit 55. An image which is received by the light receiver 45 is photoelectrically converted, then sent to the inputting unit 54, and digitized in the inputting unit 54. The digitized signal is captured by the measurement main unit 55.

The measurement main unit 55 averages digitized signals of, for example, every frame. In order to convert the value to a $CO_2$ amount (ppm), the $CO_2$ amount is obtained by using a table which is previously prepared, and then sent to the announcing unit 53. Consequently, the sensor can be easily placed, and the $CO_2$ amount can be adequately measured.

According to an aspect of the invention, the $CO_2$ sensor and $CO_2$ measuring apparatus includes: the sensing portion which changes in color in accordance with the $CO_2$ partial pressure in the expiration from the nares and/or mouth of a living body; and the mounting member which is supported by the living body to place and hold the sensing portion to a position where the expiration from the nares and/or the mouth impinges on the sensing portion. Therefore, the $CO_2$ sensor and the $CO_2$ measuring apparatus are compact in size, their power consumptions can be suppressed to a low level, and $CO_2$ measurement can be easily performed.

According to an aspect of the invention, the $CO_2$ measuring apparatus includes: the CO2 sensor; a light source which emits a light signal toward the sensing portion; a light receiver which receives the light signal from the sensing portion; and a $CO_2$ measuring unit which performs a $CO_2$ measurement based on the received light signal. Therefore, the apparatus can perform also accurate measurement by using the received light signal, can be widely applied to respiration management of the patient, and can largely contribute to safety of the patient.

What is claimed is:
1. A $CO_2$ sensor comprising:
   a sensing portion operable to change in color in accordance with a $CO_2$ partial pressure in expiration from at least one of nares and a mouth of a living body; and
   a mounting member that is capable of being supported on the living body with an adhesive portion, and adapted to detachably hold the sensing portion in a vicinity of the nares so that the expiration from the at least one of nares and a mouth impinges on the sensing portion, the adhesive portion being formed by a tape or a sheet, wherein, in the sensing portion, a chemical solution which is operable to change in color in accordance with the $CO_2$ partial pressure is held on fabric or paper or held on the mounting member, wherein the tape or the sheet has a first surface adapted to be stuck to the living body through an adhesive agent applied to the first surface and a second surface which is opposite to the first surface, wherein the sensing portion is held on the second surface and exposed at a side of the second surface, and wherein the mounting member includes:

the adhesive portion adapted to extend in a longitudinal direction of a lip of the mouth of the living body with a band-like shape adapted about the philtrum above the lip;

and a mouth cover which is integrally formed with the adhesive portion, the mouth cover including a first side adapted to face the lip and a second side adapted to face away from the lip, the mouth cover adapted to extend toward a downward direction of the lip, and includes a groove providing an airflow path adapted to extend in an up-down direction adjacent the first side of the mouth cover and an opening which faces the sensing portion at an upper end portion of the groove, a projecting piece projecting forward from a connecting portion that connects the adhesive portion and the mouth cover, located above the opening, and including a hole, and an additional sensing portion similar to the sensing portion is disposed on the projecting piece so as to close the hole.

2. The $CO_2$ sensor according to claim 1, wherein the mounting member is capable of holding the sensing portion on a philtrum of the living body.

3. A $CO_2$ measuring apparatus comprising:

the $CO_2$ sensor according to claim 1;

a light source operable to emit a light signal toward the sensing portion;

a light receiver operable to receive a light signal in response to a color of the sensing portion; and a $CO_2$ measuring unit operable to perform a $CO_2$ measurement based on the light signal received by the light receiver.

4. The $CO_2$ measuring apparatus according to claim 3, wherein the light signal received by the light receiver is a light signal reflected from or transmitted through the sensing portion.

5. The $CO_2$ measuring apparatus according to claim 3, wherein the light signal emitted from the light source includes at least two kinds of light signals having different wavelengths.

6. The $CO_2$ measuring apparatus according to claim 3, wherein an optical fiber for conducting light is disposed at least one of an area from the light source to the sensing portion and an area from the sensing portion to the light receiver.

* * * * *